United States Patent
Lamerton et al.

(10) Patent No.: US 11,229,422 B2
(45) Date of Patent: Jan. 25, 2022

(54) MICRO-NEEDLE SAMPLING DEVICE AND USE THEREOF

(71) Applicant: Global Life Sciences Solutions Operations UK Ltd., Sheffield (GB)

(72) Inventors: Kathryn Louise Lamerton, Cardiff (GB); Michael John Smith, Cardiff (GB)

(73) Assignee: Global Life Sciences Solutions Operations UK Ltd., Sheffield (GB)

(*) Notice: Subject to any disclaimer, the term of this patent is extended or adjusted under 35 U.S.C. 154(b) by 626 days.

(21) Appl. No.: 15/760,062

(22) PCT Filed: Oct. 3, 2016

(86) PCT No.: PCT/EP2016/073579
§ 371 (c)(1),
(2) Date: Mar. 14, 2018

(87) PCT Pub. No.: WO2017/055631
PCT Pub. Date: Apr. 6, 2017

(65) Prior Publication Data
US 2020/0229803 A1  Jul. 23, 2020

(30) Foreign Application Priority Data
Oct. 1, 2015 (GB) ...................... 1517373

(51) Int. Cl.
*A61B 10/02* (2006.01)
*G01N 1/08* (2006.01)
*A61M 37/00* (2006.01)

(52) U.S. Cl.
CPC .......... *A61B 10/0233* (2013.01); *G01N 1/08* (2013.01); *A61M 37/0015* (2013.01); *A61M 2037/0046* (2013.01); *A61M 2205/0238* (2013.01)

(58) Field of Classification Search
CPC ................. A61B 10/0233; G01N 1/08; A61M 2037/0046; A61M 37/0015; A61M 2205/0238
See application file for complete search history.

(56) References Cited

U.S. PATENT DOCUMENTS

2007/0060837 A1* 3/2007 Cho .................. A61M 37/0015
 600/562
2013/0144257 A1* 6/2013 Ross ................. A61M 37/0015
 604/506
2014/0287942 A1* 9/2014 Mahmood ............ A61B 5/1468
 506/9

FOREIGN PATENT DOCUMENTS

RU  2567826 C1  11/2015
WO  03/053258 A1  7/2003
(Continued)

OTHER PUBLICATIONS

Tuck Lee, K. et al. 2014. Capture of the Circulating Plasmodium falciparum Biomarker HRP2 in a Multiplexed Format, via a Wearable Skin Patch. Analytical Chemistry. 86: 10474-10483. (Year: 2014).*

(Continued)

*Primary Examiner* — William H. Beisner
(74) *Attorney, Agent, or Firm* — Eversheds Sutherland (US) LLP

(57) ABSTRACT

The present invention relates to a device (10) for obtaining a sample (30) from a biological material (40) in solid form, said device comprising an array of micro-needles (30) arranged on a base plate (20). It further relates to a method for obtaining a sample (50) from a biological material (40) in solid form, comprising pressing the micro-needles (30) of the device (10) into said biological material (40), and (Continued)

subsequently removing the device from the biological material (40), and to the use of the device (10) in such a method.

11 Claims, 4 Drawing Sheets

Specification includes a Sequence Listing.

(56) References Cited

FOREIGN PATENT DOCUMENTS

| | | |
|---|---|---|
| WO | 2007/080427 A2 | 7/2007 |
| WO | 2009080427 A1 | 7/2009 |
| WO | 2012/066506 A2 | 5/2012 |
| WO | 2013/040448 A1 | 3/2013 |
| WO | 2014/093934 A1 | 6/2014 |

OTHER PUBLICATIONS

PCT International Search Report for PCT Application No. PCT/EP2016/073579 dated Dec. 2, 2016 (8 pages).

GB Search Report for GB Application No. 1517373.5 dated Jun. 30, 2016 (4 pages).

\* cited by examiner

MICRO-NEEDLE SAMPLING DEVICE AND USE THEREOF

CROSS REFERENCE TO RELATED APPLICATIONS

This application claims the priority benefit of PCT/EP2016/073579 filed on Oct. 3, 2016 which claims priority benefit of Great Britain Application No. 1517373.5 filed Oct. 1, 2015. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on Mar. 2, 2018, is named 40145945_SL.txt and is 807 bytes in size.

FIELD OF THE INVENTION

The present invention relates to a method, a device, and the use of the device, for obtaining samples. In particular, the invention relates to sampling of solid biological materials by inserting microscopic needles into the biological material and subsequently removing them from the biological material, thereby obtaining a sample of the biological material attached to the needles.

BACKGROUND OF THE INVENTION

Nucleic acid sample preparation begins with the process of sample collection. If samples are not collected and handled properly, it may be impossible to obtain high-quality nucleic acid regardless of the method used for DNA preparation. Therefore, sample collection is critical to obtaining optimal results in downstream applications for nucleic acids.

Collection of samples of biological material for diagnostic or forensic purposes may be performed in various ways, and often includes drawing of blood by venepuncture or finger prick. These methods involve pain to the subject and a significant number of subjects feel discomfort with these methods. Some subjects may also have a severe fear or phobia related to the pain involved and/or the drawing of blood which may entail avoidance of these procedures. This in turn may lead to subjects not seeking medical care when they are in need of such care, and to healthcare providers not having sufficient information to make correct diagnoses.

Collection of samples of biological material for forensic purposes are usually done with buccal swabs. However, the number of cells collected with the swab varies and depends on a variety of factors including the technique of the person taking the swab, whether the donor is a high or low shedder, and the type of swab used. Also the efficiency in the transfer of cells from the swab to a storage medium varies.

Micro-needle devices for application on the human or animal skin have been suggested for various applications including drug delivery and cosmetics.

Devices for transdermal delivery of various drugs usually comprise hollow micro-needles wherein the drug is delivered into the epidermis or dermis of the patient through the hollow cavity in the micro-needle. One example of such a system is the Hollow Microstructured Transdermal System available from 3M (S:t Paul, Minn., U.S.). Sullivan and co-workers (Sullivan et al. *Nature Medicine* 16, 915-920 (2010)) have proposed dissolving micro-needle patches for influenza vaccination using a patch-based system, wherein influenza virus vaccine contained in the micro-needles was delivered during a dissolution of the micro-needle when applied to the patient's skin.

Patches comprising arrays of micro-needles and intended for use as transdermal devices are commercially available from i.a. Innoture Medical Technology, Ltd. (London, U.K.). Cylinders comprising an array of micro-needles on the cylinder surface are sold for cosmetic purposes under the trademark Dermaroller®.

Fabrication of micro-needles and patches comprising arrays of micro-needles is well-known in the art and described for example in WO2006/018642 and WO2007/080427.

SUMMARY OF THE INVENTION

There exists a need in the art for an alternative device and method for sample collection that is non-invasive and less painful than venepuncture or finger prick, but nevertheless can obtain live/viable cells from the epidermis or dermis. There also exists a need for an alternative device and method for sample collection that is consistent in obtaining the sample and transferring it to a storage medium, and preferably also negate the need to put a swab into someone's mouth, which may be uncomfortable for both the person providing the sample and the person taking the sample.

The present invention thus proposes the use of micro-needle technology for sample collection, i.e., the collection of cells from the skin for forensic or diagnostic analyses and the possible collection of cells from the surface of tissue samples (fresh, frozen or Formalin Fixed, Paraffin Embedded (FFPE)) prior to applying to solid media. After removal the micro-needle device could be applied to a solid medium to preserve the biological sample and stabilise the DNA, RNA, protein etc. prior to transportation and storage.

DETAILED DESCRIPTION OF THE INVENTION

Figure 1:
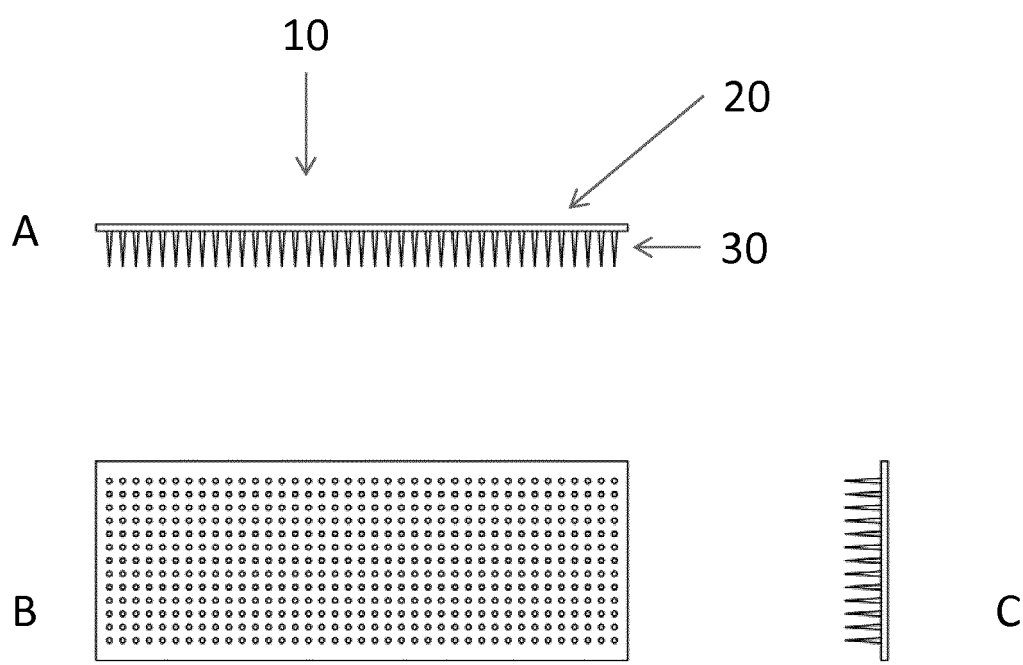
FIG. 1 shows a a side view (A) of an exemplary device (10) according to the invention, said device comprising a base plate (20) having an array of micro-needles (30) arranged thereon. The figure also shows a view of the array side (B) of the device, and a side view (C) of the device.

In one aspect, the present invention relates to a device for obtaining a sample from a biological material in solid form, wherein the device comprises an array of micro-needles arranged on a base plate. This is shown in FIG. 1, wherein an exemplary device (10) comprising a base plate (20) having an array of micro-needles (30) arranged thereon is shown.

The micro-needles arranged on the base plate may be solid. However, hollow micro-needles of the type used in some types of drug delivery may be used also in the present invention. The micro-needles may also have a rugged or generally uneven surface in order to increase the surface area of the micro-needle in order to increase the amount of biological material that may adhere to the micro-needle. It is also contemplated that the micro-needles may be porous so that biological material may diffuse into the micro-needle to further increase the amount of biological material that adheres to the micro-needle.

The base plate (10) is typically made of a flexible material for ease of application to the surface of a biological material, such as the skin of a human or animal subject. The base plate and the micro-needles may be made from the same or different material. Suitable materials for manufacture of the base plate and/or the micro-needles are from silica; polymers, such as epoxy resins, acrylic polymers, polyurethane, polypropylene, and silicone resins; ceramics; metal; or a combination thereof.

The micro-needles are generally of a length in the micrometer range, i.e. from 1-10 micrometers up to a 1 or 2 milimeters. The length of the micro-needles may be adapted to be long enough to penetrate through the strateum corneum and into the epidermis of a subject to which the micro-needles are applied when in use. Typical lengths of micro-needles may be 0.1-1.5 mm preferably 0.15-1.0 mm, such as 0.2-0.5 mm. The concentration of micro-needles on the base plate is typically in the range 400-12,000 micro-needles per $cm^2$, such as 1,000, 2,000, 3,000, 4,000, 5,000, 6,000, 7,000, 8,000, 9,000, 10,000, or 11,000 micro-needles per $cm^2$.

The micro-needles may have an average diameter of 0.1-0.3 mm and be in the shape of cones, three-sided or four-sided pyramids, or rods with conical or pyramidal tips, extending from the base plate.

Figure 2:
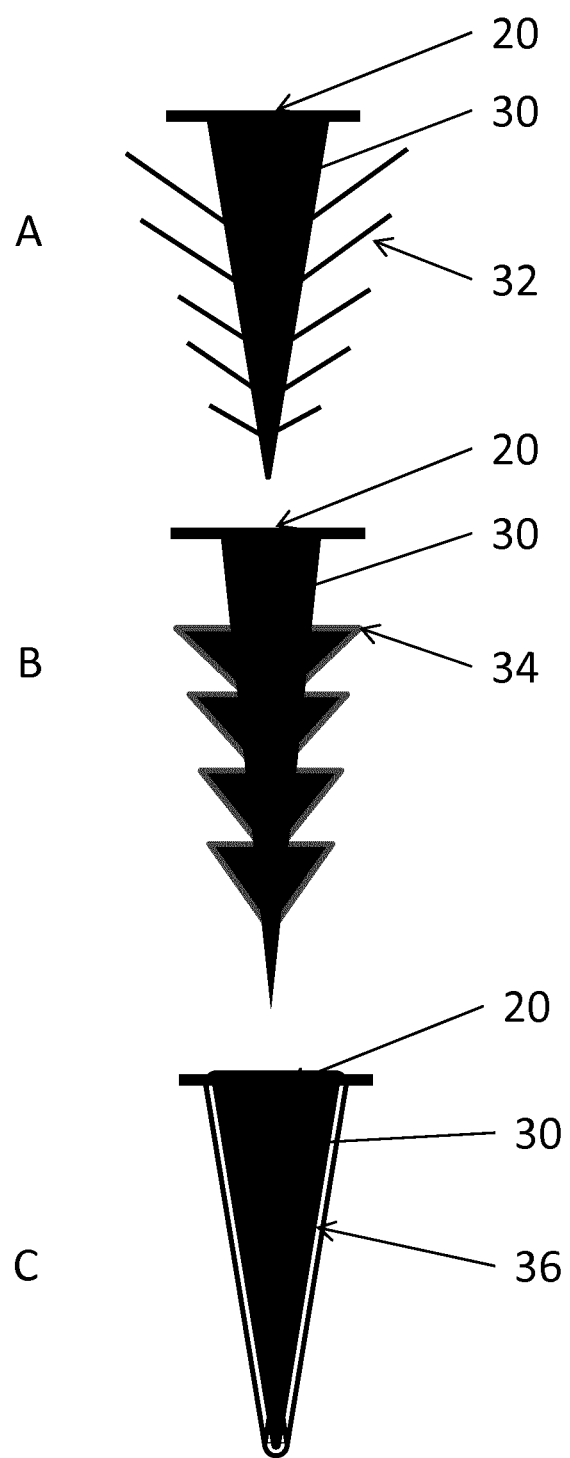
FIG. 2 illustrates individual micro-needles (30) having surface modifications (32, 34, 36). (A) a micro-needle (30) with protrusions in the form of bristles (32). (B) a micro-needle (30) with protrusions in the form of barbs (34). (C) a micro-needle with a coating (36).

The micro-needles may also have a barbed or rugged surface. An embodiment wherein the micro-needles are equipped with bristles (32) is shown in FIG. 2 A. An embodiment wherein the micro-needles are equipped with barbs (34) is shown in FIG. 2 B.

The micro-needles may also be coated with a coating (36) enhancing adherence of biological material, such as cells, proteins, and/or nucleic acids including DNA, to the micro-needles. Such coatings may be selected from extracellular matrix attachment proteins, extracellular matrix adhesion proteins, mucopolysaccharides, basic synthetic polymers, or any combination thereof. Examples of coatings that may be suitable for use with the present invention are collagen, laminin, fibronectin, from heparin sulfate, hyaluronidate, chondroitin sulfate, and poly-D-lysine.

Figure 3:
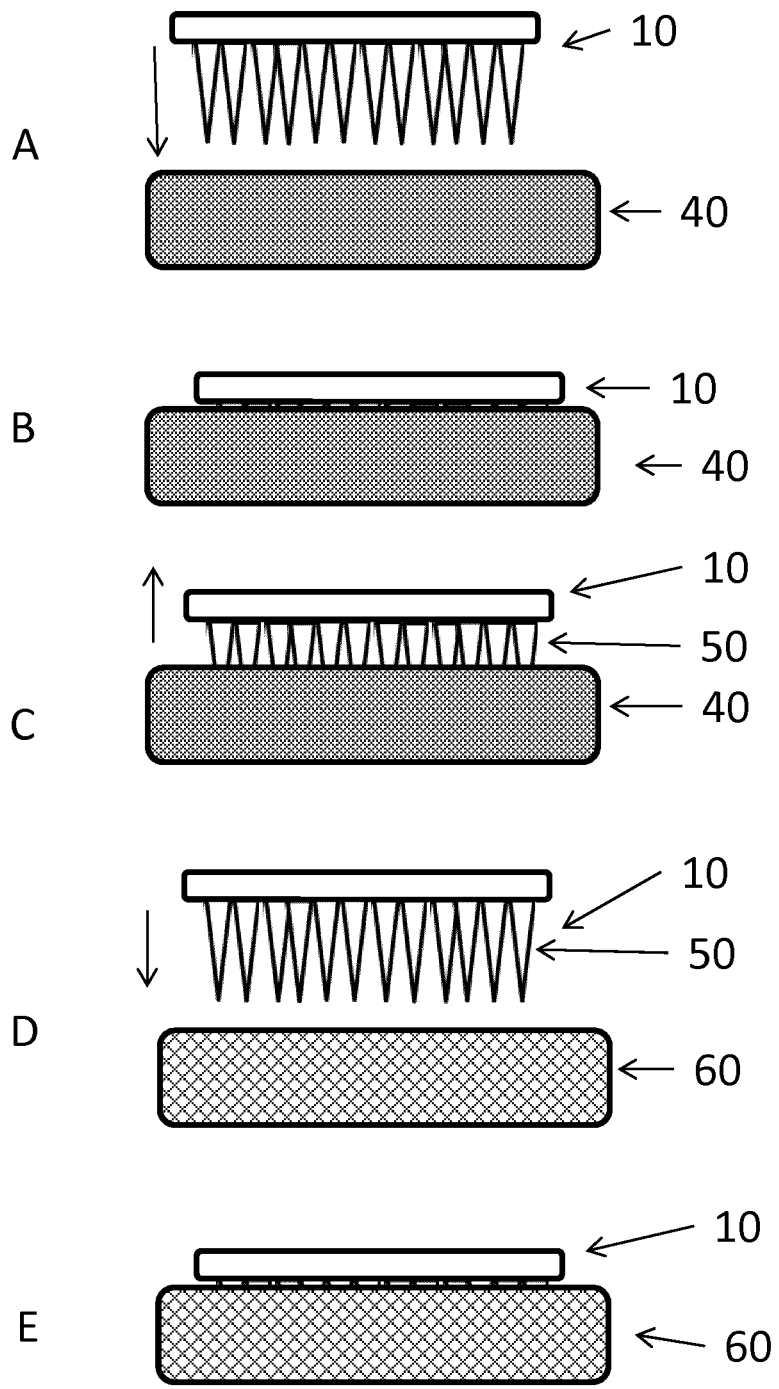
FIG. 3 illustrates a workflow for using a micro-needle device(10) in obtaining a sample from a biological material (40) and transferring it to a solid medium (50) for further processing.
Figure 4:
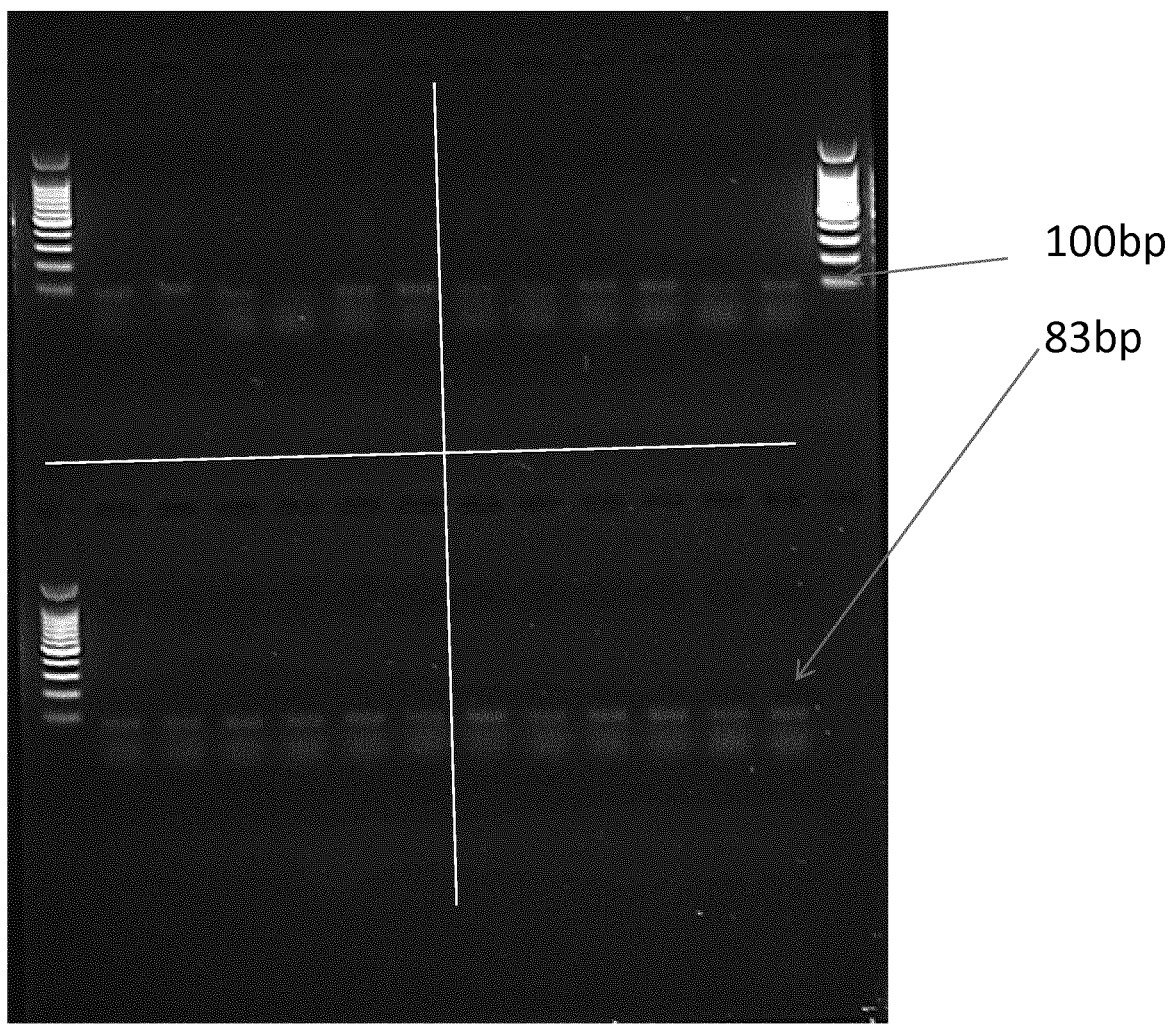
FIG. 4: Endpoint PCR showing 85 bp amplicon amplified from bovine gDNA applied to FTA micro-cards using a foam-tipped swab and commercially available micro-needle roller systems with varying needle length. Upper Left: 0.5 mm micro-needle; Upper Right: 0.2 mm micro-needle; Lower Left: Swab; Lower Right: 1.0 mm micro-needle.

In a further aspect, the invention relates to a method for obtaining a sample (50) from a biological material (40) in solid form, comprising pressing the micro-needles (30) of a device (10) according to the above aspect, into said biological material (40), and subsequently removing the device from the biological material (40). Part of the biological material (40), including whole cells, proteins, and/or nucleic acids including DNA, will adhere to the micro-needles (30) and thus constitute the sample (50). This workflow is shown in FIG. 3 (A)-(C).

The biological material (40) may be the skin from a living or deceased human or animal, or a fresh, frozen, or Formalin Fixed, Paraffin Embedded (FFPE) tissue sample. The sample (50) obtained from the biological material (40) thus typically comprise whole cells, proteins, and/or nucleic acids including DNA, and may originate from the subject from which the biological material originates or from foreign organisms such as microbes.

In a preferred embodiment, the sample of biological material is transferred to a solid medium (60) for storage of samples of biological material, by pressing the micro-needles (30) into the solid medium (60). This workflow is shown in FIG. 3 (D)-(E).

Such media for storage of samples of biological material are well-known in the art and include 903 Sample Collection Cards, Whatman FTA/FTA Elute Sample Collection Cards, and DMPK Sample Collection Cards, all available from GE Healthcare, Uppsala, Sweden. Whatman FTA technology is a patented process that incorporates chemically coated matrices to collect, transport, archive and isolate nucleic acids in a single device. The technology, which consists of two distinct chemistries for FTA and FTA Elute, has the ability to lyse cells on contact, denature proteins, and protect DNA from degradation caused by environmental challenges and microbial attack. FTA contains chemical denaturants and a free radical scavenger, while FTA Elute contains a chaotropic salt. The difference in the chemical coatings is what allows the DNA to be eluted from FTA Elute into a solution phase, while purified DNA remains bound to FTA. Purified genomic DNA from FTA and FTA Elute is suitable for use in PCR, STR, SNP genotyping, allelic discrimination genotyping, and RFLP analyses. DNA from FTA is also suitable for AFLP; DNA from FTA Elute is also suitable for use in TaqMan™ assays.

Samples may thus be collected onto FTA or FTA Elute cards by pressing the micro-needles into the cards, and cards are dried. Discs of FTA and FTA Elute are removed from sample areas using a coring device, such as a Harris Micro Punch or Uni-Core. These coring devices come in various sizes (i.e., 1.2 mm, 2.0 mm, and 3.0 mm); the choice of size depends on both the downstream application and the initial sample type. For applications that require DNA in solution, multiple discs can be treated at once. Genomic DNA purification from sample applied to FTA cards may be performed according to the manufacturer's instructions.

The invention also relates to the use of a device according to the first aspect in a method according to the second aspect.

SEQUENCES

The following sequences are included in the attached sequence listing.

```
Forward primer:
                                          (SEQ ID NO: 1)
CTAAGATCATGGCATCAGGTCC Reverse primer:
                                          (SEQ ID NO: 2)
CCCCAAAATAAAGTCAGCCAC FAM TAM probe:
                                          (SEQ ID NO: 3)
[6FAM]TCCACTGTTTCCCCATCTATTTGCCA[TAM]
```

EXAMPLE

The invention is further illustrated in the example below. The examples are not intended to limit the invention, which is defined in the appended claims.

The principle of the invention is shown in this example by analysis of samples obtained from bovine meat with the use of a micro-needle device.

Materials:
FTA cards: GEHC WB120055 #9463630 (GE Healthcare, Uppsala, Sweden)
Indicating FTA cards: GEHC WB120211 #384045 (GE Healthcare, Uppsala, Sweden)
Foam tipped swabs, GEHC WB100032 #3673(GE Healthcare, Uppsala, Sweden)
Sirloin steak (obtained from the local supermarket)
Bovine genomic DNA. AMSBIO cat: D1634999-G01 #B601033
Primers and probes (obtained from Sigma-Aldrich)

```
Forward:
                                    (SEQ ID NO: 1)
CTAAGATCATGGCATCAGGTCC Reverse:
                                    (SEQ ID NO: 2)
CCCCAAAATAAAGTCAGCCAC FAM TAM probe:
                                    (SEQ ID NO: 3)
[6FAM]TCCACTGTTTCCCCATCTATTTGCCA[TAM]
```

Applied Biosystems: 2× Taqman Universal PCR Master Mix cat:4324018 #1406029, exp October 2015
Sterile water
Derma roller 0.2 mm: MT roller, Model MT2 (no other details supplied)
Derma roller 0.5 mm: Dermaroller System (DRS), model DRS50 (no other details supplied)
Derma roller 1.0 mm: Micro Needle Roller System, model MR100, RoHS ref JMF-003, lot: 130348, Exp March 2015.
2 mm Harris micro-punch
Applied Biosystems real-time 7900 QPCR machine, CL/LE/PE/00293, calibration due September 2015.

Method

Real-time detection and quantification of bovine DNA were performed essentially as described in Cai et al., Journal of Food Composition and Analysis, 25 (2012) pp. 83-87.

Samples were obtained from the bovine meat using micro-needles of length 0.2 mm, 0.5 mm or 1.0 mm, or a swab, and transferred to a FTA card, and also using micro-needles of length 0.5 mm or a swab and transferred onto an indicating FTA card. All samples were repeated six times, as set out in the table below.

TABLE 1

| Sample ID | Details |
|---|---|
| 1 | 0.5 mm micro-needle onto FTA |
| 2 | |
| 3 | |
| 4 | |
| 5 | |
| 6 | |
| 7 | Swab onto FTA |
| 8 | |
| 9 | |
| 10 | |
| 11 | |
| 12 | |
| 13 | 0.2 mm micro-needle onto FTA |
| 14 | |
| 15 | |
| 16 | |
| 17 | |
| 18 | |
| 19 | 1.0 mm micro-needle onto FTA |
| 20 | |
| 21 | |
| 22 | |
| 23 | |
| 24 | |
| 25 | 0.5 mm micro-needle onto indicating FTA |
| 26 | |
| 27 | |
| 28 | |
| 29 | |
| 30 | |
| 31 | Swab onto indicating FTA |
| 32 | |
| 33 | |
| 34 | |
| 35 | |
| 36 | |

Day 1: For micro-needle application, the dermaroller was placed on the fresh joint of beef (not rolled) and then pressed onto the FTA paper. For swab application, the swab head was rolled back & forth 4 times on the joint of beef, then applied to the FTA paper & rolled back & forth 4 times. Post application samples were left to dry in a laminar flow cabinet for >3 hours, then stored in a desiccator cabinet overnight.

Day 2:
1. Dilute primers to give 250 nM in PCR reaction (20 ul):
   Dilute supplied primers to 100 uM as follows:
      Forward primer (supplied at 37.9 nmol)—add 379 ul sterile water to give 100 uM solution.
      Reverse primer (supplied at 37.2 nmol)—add 372 ul sterile water to give 100 uM solution.
   For each primer—dilute to 2.5 uM as follows:
      100 uM/2.5 uM=1:40 dilution
      Add 5 ul 100uM solution to 195 ul sterile water
2. Dilute probe to give 500 nM in PCR reaction (20 ul)
   Dilute supplied probe to 100 uM as follows:
      Probe (supplied at 13.2 nmol)—add 132 ul sterile water to give 100 uM solution.
   Dilute probe to 5 uM as follows:
      100 uM/5 uM=1:20 dilution
      Add 10 ul 100 uM solution to 190 ul sterile water
3. Preparation of standard curve:
   Stock=1.10 ug/ml (i.e., 1100 pg/ul)
   Dilute bovine gDNA to 50 pg/ul as follows:
   1100/50=1:22 dilution
   Add 10 ul stock to 210 ul sterile water to give 50 pg/ul=100 pg/2 ul
   Prepare 1:10 dilutions (10 ul+90 ul sterile water) to give the following standard curve solutions:
      1. 100 pg/2 ul
      2. 10 pg/2 ul
      3. 1 pg/2 ul
      4. 0.1 pg/2 ul
      5. 0.01 pg/2 ul
      6. 0.001 pg/2 ul
4. Preparation of FTA punches:
   2 mm punches (using a Harris punch) were removed from bovine-spotted FTA punches and transferred to sterile 0.5 ml eddpendorf tubes.
   Each punch was washed 3× using 200 ul GEHC FTA purification reagent, then 2× using 200 ul 1× TE buffer (0.01M Tris, 0.001M EDTA, pH 7.4).

Punches were left to dry for ~30 mins prior to using in direct QPCR reactions as below:

5. Gel Electrophoresis:

Pour a 1× TAE, 1% agarose gel:
  a) Weigh out 1 g agarose in a sterile erlenmeyer flask
  b) Add 100 ml 1× TAE buffer (Tris-Acetate/EDTA)
  c) Heat in a microwave, heat for 1 minute, mix, then further 30 sec intervals until the agarose has dissolved
  d) Leave to cool for ~2 minutes, then add 10 ul Gel Red stain
  e) Pour into gel tray, avoid air bubble formation, insert gel combs and leave to dry for ~30 mins To load PCR samples:
  a) Fill the gel tank with 1× TAE buffer (remove the 'stoppers' used to cast the gel)
  b) Add 4 ul of 6× loading dye to 15 ul PCR reactions and load between 10 ul into each well of the gel
  c) Load DNA markers into 1 lane of the gel.
  d) Connect the electrophoresis tank to the power & run at ~80 volts for ~30-40 mins A resulting gel is shown in FIG. 3. Endpoint PCR showing 85 bp amplicon amplified from bovine gDNA applied to FTA micro-cards using a foam-tipped swab and commercially available micro-needle roller systems with varying needle length. Upper Left: 0.5 mm micro-needle; Upper Right: 0.2 mm micro-needle; Lower Left: Swab; Lower Right: 1.0 mm micro-needle. A 100 bp DNA ladder were run in upper and lower leftmot lanes, and the upper rightmost lane. The 83 bp fragment is highlighted in FIG. 3. Primer dimers are visible below the 83 bp fragment.

PCR reaction

TABLE 2

| Reagent/concentration | Volume (ul) |
| --- | --- |
| Forward primer @ 2.5 uM | 2 |
| Reverse primer @ 2.5 uM | 2 |
| Probe @ 5.0 uM | 2 |
| 2X PCR Master Mix | 10 |
| Water | 4 |
| 2 mm punch | x1 |
| Final volume | 20 |

TABLE 3

| Reagent/concentration | Volume (ul) |
| --- | --- |
| Forward primer @ 2.5 uM | 2 |
| Reverse primer @ 2.5 uM | 2 |
| Probe @ 5.0 uM | 2 |
| 2X PCR Master Mix | 10 |
| Water | 2 |
| Control bovine gDNA @ 1 ng/ul | 2 |
| Final volume | 20 |

TABLE 4

| PCR cycling conditions | | |
| --- | --- | --- |
| 1. Initial denaturation | 50° C. | 2 min |
| 2. Initial denaturation | 95° C. | 10 min |
| 3. Denaturation | 95° C. | 15 sec |
| 4. Anneal, elongate | 60° C. | 1 min |
| Repeat steps 3 & 4 × 40 times | | |

TABLE 5

| | Plate map | | | | | | | | | | | |
| --- | --- | --- | --- | --- | --- | --- | --- | --- | --- | --- | --- | --- |
| | 1 | 2 | 3 | 4 | 5 | 6 | 7 | 8 | 9 | 10 | 11 | 12 |
| A | 100 pg/well | | | Punches from 0.5 mm micro-needle (samples 1 to 6) | | | | | | Empty | Empty | Empty |
| B | 10 pg/well | | | Punches from swab (samples 7 to 12) | | | | | | Empty | Empty | Empty |
| C | 1 pg/well | | | Punches from 0.2 mm micro-needle (samples 13 to 18) | | | | | | Empty | Empty | Empty |
| D | 0.1 pg/well | | | Punches from 1.0 mm micro-needle (samples 19 to 24) | | | | | | Empty | Empty | Empty |
| E | 0.01 pg/well | | | No Template Control | | | Empty | Empty | Empty | Empty | Empty | Empty |
| F | 0.01 pg/well | | | Empty | Empty | Empty | Empty | Empty | Empty | Empty | Empty | Empty |
| G | 10 pg/ well + blank punch | 10 pg/ well + blank punch | 10 pg/ well + blank punch | Empty | Empty | Empty | Empty | Empty | Empty | Empty | Empty | Empty |
| H | | | | Empty | Empty | Empty | Empty | Empty | Empty | Empty | Empty | Empty |

Results

The results are summarized in Table 6

TABLE 6

| Well | Sample Name | Ct | Quantity (pg/ul) | Quantity (pg/ml) |
| --- | --- | --- | --- | --- |
| 4 | 0.5 mm miconeedle | 20.601551 | 1.0145711 | 1014.571 |
| 5 | 0.5 mm miconeedle | 26.268627 | 0.014150693 | 14.151 |
| 6 | 0.5 mm miconeedle | 33.313503 | 6.98E−05 | 0.070 |
| 7 | 0.5 mm miconeedle | 35.29981 | 1.56E−05 | 0.016 |
| 8 | 0.5 mm miconeedle | 29.670776 | 0.001088558 | 1.089 |
| 9 | 0.5 mm miconeedle | 26.111387 | 0.015931653 | 15.932 |
| 16 | Swab | 26.547935 | 0.011463758 | 11.464 |
| 17 | Swab | 31.232628 | 3.35E−04 | 0.335 |
| 18 | Swab | 27.237637 | 0.006815631 | 6.816 |
| 19 | Swab | 27.346052 | 0.006280713 | 6.281 |
| 20 | Swab | 24.847023 | 0.04132729 | 41.327 |
| 21 | Swab | 25.545555 | 0.02440758 | 24.408 |

TABLE 6-continued

| Well | Sample Name | Ct | Quantity (pg/ul) | Quantity (pg/ml) |
|---|---|---|---|---|
| 28 | 0.2 mm micro-needle | 29.195902 | 0.001557163 | 1.557 |
| 29 | 0.2 mm micro-needle | 1.1531498 | 2366172 | 2366172000 |
| 30 | 0.2 mm micro-needle | 27.272406 | 0.006639297 | 6.639 |
| 31 | 0.2 mm micro-needle | 28.55655 | 0.002521564 | 2.522 |
| 32 | 0.2 mm micro-needle | 39.614628 | 6.04E−07 | 0.001 |
| 33 | 0.2 mm micro-needle | 37.7316 | 2.50E−06 | 0.002 |
| 40 | 1 mm micro-needle | 22.972874 | 0.16977271 | 169.773 |
| 41 | 1 mm micro-needle | 28.513432 | 0.002604879 | 2.605 |
| 42 | 1 mm micro-needle | 26.627182 | 0.010798915 | 10.799 |
| 43 | 1 mm micro-needle | 34.065872 | 3.96E−05 | 0.040 |
| 44 | 1 mm micro-needle | Undetermined | 0 | 0.000 |
| 45 | 1 mm micro-needle | 33.36794 | 6.70E−05 | 0.067 |
| 52 | No template control | Undetermined | 0 | 0 |
| 53 | No template control | Undetermined | 0 | 0 |
| 54 | No template control | Undetermined | 0 | 0 |
| 13 | 10 pg/ul | 17.68969 | 10 | 10000.000 |
| 14 | 10 pg/ul | 17.678354 | 10 | 10000.000 |
| 15 | 10 pg/ul | 17.447315 | 10 | 10000.000 |
| 73 | punch + 10 pg/ul | 19.211739 | 2.8928947 | 2892.895 |
| 85 | punch + 10 pg/ul | 17.58295 | 9.877061 | 9877.061 |
| 37 | 0.1 pg/ul | 23.980858 | 0.1 | 100.000 |
| 38 | 0.1 pg/ul | 23.688795 | 0.1 | 100.000 |
| 39 | 0.1 pg/ul | 23.7168 | 0.1 | 100.000 |
| 74 | punch + 0.1 pg/ul | 23.077671 | 0.15687558 | 156.876 |
| 86 | punch + 0.1 pg/ul | 23.667562 | 0.10055739 | 100.557 |
| 49 | 0.01 pg/ul | 26.331987 | 0.01 | 10.000 |
| 50 | 0.01 pg/ul | 26.249264 | 0.01 | 10.000 |
| 51 | 0.01 pg/ul | 26.419891 | 0.01 | 10.000 |
| 61 | 0.001 | 30.151587 | 0.001 | 1.000 |
| 62 | 0.001 | 29.975388 | 0.001 | 1.000 |
| 63 | 0.001 | 29.93187 | 0.001 | 1.000 |
| 75 | punch + 0.001 pg/ul | 29.214556 | 0.001535418 | 1.535 |
| 87 | punch + 0.001 pg/ul | 30.067472 | 8.0717E−04 | 0.807 |

The average quantity of DNA obtained from the biological material is, with the outliers of wells 4 and 29 removed:

TABLE 7

| | |
|---|---|
| 0.2 mm micro-needle | 2.144225 pg/ml |
| 0.5 mm miconeedle | 6.251275 pg/ml |
| 1 mm micro-needle | 30.547192 pg/ml |
| Swab | 15.10505 pg/ml |

These results demonstrate that microneedles can be used to obtain sufficient DNA for QPCR analysis, using a device with micro-needles of a length of 0.2, 0.5, or 1 mm.

The invention claimed is:

1. A method for obtaining a sample from a biological material in solid form for storage on a solid medium, comprising pressing micro-needles of a device into said biological material, characterized in said device comprising an array of micro-needles arranged on a base plate, wherein the micro-needles are coated with a coating enhancing adherence of biological material to the micro-needles, wherein said coating is selected from extracellular matrix attachment and/or adhesion proteins, mucopolysaccharides, basic synthetic polymers, or any combination thereof, and subsequently removing the device from the biological material and transferring the sample of the biological material to said solid medium by pressing the micro-needles into the solid medium.

2. The method according to claim 1, wherein the micro-needles are solid.

3. The method according to claim 1, wherein the micro-needles have a length of 0. 1-1.5 mm.

4. The method according to claim 1, wherein the micro-needles have an average diameter of 0.1-0.3 mm.

5. The method according to claim 1, wherein the micro-needles are in the shape of cones, pyramids, or rods with conical or pyramidal tips, pointing upward from the base plate.

6. The method according to claim 1, wherein the micro-needles have a barbed or rugged surface.

7. The method according to claim 1, wherein the coating comprises extracellular matrix attachment and/or adhesion proteins selected from collagen, laminin and fibronectin; mucopolysaccharides selected from heparin sulfate, hyaluronidate and chondroitin sulfate; basic synthetic polymers selected from poly-D-lysine; or any combination thereof.

8. The method according to claim 1, wherein the concentration of the micro-needles on the base plate is 400-12,000 micro-needles per $cm^2$.

9. The method according to claim 1, wherein the base plate is made of a flexible material.

10. The method according to claim 1, wherein the micro-needles and the base plate are made of the same or different material.

11. The method according to claim 1, wherein the micro-needles and/or the base plate are made of a material selected from silica, epoxy resins, acrylic polymers, polyurethane, polypropylene, silicone resins, ceramics, metal, or a combination thereof.

* * * * *

SEQUENCE LISTING

<160> NUMBER OF SEQ ID NOS: 3

<210> SEQ ID NO 1
<211> LENGTH: 22
<212> TYPE: DNA
<213> ORGANISM: Bos taurus

<400> SEQUENCE: 1
ctaagatcat ggcatcaggt cc      22

<210> SEQ ID NO 2
<211> LENGTH: 21
<212> TYPE: DNA
<213> ORGANISM: Bos taurus

<400> SEQUENCE: 2
ccccaaaata aagtcagcca c      21

<210> SEQ ID NO 3
<211> LENGTH: 26
<212> TYPE: DNA
<213> ORGANISM: Bos taurus
<220> FEATURE:

-continued

```
<221> NAME/KEY: misc_feature
<222> LOCATION: (1)..(1)
<223> OTHER INFORMATION: 6-carboxyfluorescein
<220> FEATURE:
<221> NAME/KEY: misc_feature
<222> LOCATION: (26)..(26)
<223> OTHER INFORMATION: tetramethylrhodamine

<400> SEQUENCE: 3
tccactgttt ccccatctat ttgcca                                           26
```